United States Patent [19]
Schöning et al.

[11] Patent Number: 5,874,047
[45] Date of Patent: Feb. 23, 1999

[54] CHEMICAL SENSORS, IN PARTICULAR SILICON-BASED BIOSENSORS

[75] Inventors: Michael Josef Schöning, Jülich; Marion Thust, Köln; Stephan Frohnhoff; Michael Götz Berger, both of Darmstadt; Rüdiger Arens-Fischer, Essen; Peter Kordos, Jülich; Hans Lüth, Aachen, all of Germany

[73] Assignee: Forschungszentrum Julich GmbH, Julich, Germany

[21] Appl. No.: 793,030

[22] PCT Filed: Aug. 4, 1995

[86] PCT No.: PCT/DE95/01056

§ 371 Date: Feb. 5, 1997

§ 102(e) Date: Feb. 5, 1997

[87] PCT Pub. No.: WO96/05512

PCT Pub. Date: Feb. 22, 1996

[30] Foreign Application Priority Data

Aug. 6, 1994 [DE] Germany ............... 44 27 921.3

[51] Int. Cl.⁶ .................................. G01N 27/26
[52] U.S. Cl. .................. 422/82.02; 422/82.03; 422/204; 422/416
[58] Field of Search ............ 422/82.02, 82.03, 422/83.04, 90, 98; 204/400, 403, 416

[56] References Cited

U.S. PATENT DOCUMENTS

| | | | |
|---|---|---|---|
| 5,063,164 | 11/1991 | Goldstein | 436/169 |
| 5,111,221 | 5/1992 | Fare et al. | 357/25 |
| 5,393,401 | 2/1995 | Knoll | 204/418 |
| 5,618,493 | 4/1997 | Goldstein et al. | 422/57 |

FOREIGN PATENT DOCUMENTS

| | | |
|---|---|---|
| 41 15 414 A1 | 11/1992 | Germany . |
| 61-218933 | 9/1986 | Japan . |
| 61218932 | 9/1986 | Japan . |
| WO 90/12092 | 10/1990 | WIPO . |

*Primary Examiner*—Jeffrey Snay
*Attorney, Agent, or Firm*—Herbert Dubno

[57] ABSTRACT

A three-dimensional structure of porous silicon considerably improves the anchorage of sensor-active material such as, for example, enzymes, antibodies, etc., on or in the substrate surface of chemical sensors, in particular silicon-based biosensors. This structure is produced by means of suitable etching which forms pore apertures adapted to the penetrability of the sensor-active material. The pore walls advantageously receive a non-conductive boundary layer which consists of oxides of Si and/or Al or Ta or silicon nitride and are preferably 1–100 nm thick. The porous layer is advantageously between 10 nm and 100 μm thick and the pores are preferably in the form of branched ducts whose average diameter is 1 nm–10 μm and in particular 10–1000 nm. The sensor-active material can optionally be distributed in a glass, solid, plastics or polymer membrane.

11 Claims, 5 Drawing Sheets

CHEMICAL SENSORS, IN PARTICULAR SILICON-BASED BIOSENSORS

SPECIFICATION

CROSS REFERENCE TO RELATED APPLICATIONS

This application is a national stage of PCT/DE95/01056 filed Aug. 9, 1995 and based, in turn, on German National application P4427921.3 filed Aug. 6, 1994 under the International Convention.

FIELD OF THE INVENTION

The invention relates to chemical sensors, in particular biosensors, which are silicon-based with a sensor-active coating on a semiconductive substrate functioning as a transducer.

BACKGROUND OF THE INVENTION

Chemical sensors and, especially biosensors operating with bioactive components are known and are the subject of vigorous development.

Such sensors basically include a surface layer with a sensor-active material which is exposed to the medium to be tested, especially a liquid. This layer contains the sensor-active material which can be immobilized, for example, in a membrane composed of polyvinylchloride. The signals supplied by the sensor-active material under the effect of an analyte are transformed by a transducer element and are acquired in registrable form by electronic signal processing which can be provided by integrated electronics.

As transducers, particularly semiconductive electrodes, field-effect transistors, potentiometric and amperometric electrodes and the like are considered.

All known sensors have the common characteristic that they generally have insufficient adhesion of the sensor membrane on the respective base element, i.e. the measurement solution can wash it away or penetrate in a detrimental manner directly into the sensor membrane and damage it irreversibly. Connected therewith are stability problems and drift problems with respect to the sensor output signals. Furthermore, there is the need to establish the out-diffusion, i.e. the bleeding or washing out, of sensitive membrane components into the solution. Such sensors, as a consequence have only a limited life. It is also a drawback that the contacts and signal electronics are only separated by a thin passivation layer from the sensitive region and thus the sensor is highly prone to damage.

An attempt to solve this problem is described by Knoll in DE 41 15 414 A1. Here, anisotropic etch pits are incorporated in the substrate material as containments in which the sensor membrane can be anchored. The containments can be jacketed in a nonconductive material and additionally, conductive electrodes can be deposited. These vertical containments comprise openings converging toward the rear side of the chips which are in direct contact with the measurement solution. As a consequence, the above-described drawbacks are overcome. Especially so-called sensor arrays can be realized with this technique with different sensitivities to different substances or ion types.

With this kind of sensor, the containment formation affords a certain protection of the ion selective membrane to limit bleeding out and dissolution. This technology is however only apparently simple in that it can be realized only with expensive lithography techniques.

OBJECT OF THE INVENTION

It is an object of the invention, therefore, to provide a sensor of the initially described type, by which the sensor-active material can be deposited in different forms on a different types of transducer/electronic structures of the sensor with reduced tendency toward damage, with stability enhancement and sensitivity increase.

SUMMARY OF THE INVENTION

This object is achieved with a silicon-based biosensor with a sensor-active coating on a semiconductor substrate effective as a transducer. According to the invention the sensor-active material is received in the pores of a porous layer produced by an etching treatment of the substrate surface and whose opening widths are matched to the penetration characteristics of the sensor-active material. A nonconducting boundary layer can be provided on the pore walls. The boundary layer between the surfaces of the porous material and the sensor-active material of silicon dioxide and/or aluminum oxide, tantalum pentoxide or silicon nitride. The nonconducting boundary layer can have a thickness of 1–100 nm. The porous layer can be a sponge-like layer with mesopores and/or macro pores. The pores can be formed as passages with branches with a mean pore diameter of 1 nm–10 µm, especially 10–1000 nm. The thickness of the foam-like layer can be 10 nm–100 µm. The active material can be an adsorptive sensor-active material incorporated in or on the foam structure and bonded by a covalent bonding of the sensor-active material to the porous layer structure.

There can also be a cross-linking of the biomolecules of the sensor-active material engaged in the pores. The sensor-active material can be distributed within a layer former such as a glass or solid or plastic or polymer member. The sensors of the invention can be ion-selective electrodes, capacitive field effect structures, ion sensitive field effect transistors, or an array of elements of different sensitivity. These sensors are especially realizable in miniatured form.

According to the invention the use porous layer eliminates the need for expensive lithography. The produced three-dimensional sponge structure serves as a matrix for a good mechanical anchoring and spatial cross-linking of the sensor-active materials in the porous semiconductor substrate. One can thus achieve a high physical (mechanical) and electromechanical stability under liquid. This permits the use of the sensor especially in throughflow operations, for example, as a detector in an FIA system.

Indeed the generation of porous silicon by an etching treatment has long been known as is also its use in biosensor technology according to JP 61-218 932 A from 1986. In this system an ISFET is described on whose surface, between source and drain, an insulating layer is generated and then coated with polycrystalline silicon, which by anodic treatment is converted into a porous silicon layer with a "film" for a biochemical substance. This proposal has not found effect in the improved formation of biosensors and has not been used in practice as can be understood from the proposal of Knoll. The present invention differs from the subject of this Japanese open application in that the semiconductor substrate effective as the transducer is directly subjected to an etching treatment to generate a porous sponge structure opening from the surface into the material, whose pores have a mean pore diameter which matches the penetration requirements for the sensor-active material.

Preferably sponge-like porous layers with mesopores and/or macropores receive the sensor-active material, especially via the intermediary of a nonconductive insulating layer of reduced thickness, such that the effectivity of the sensor-active material per unit area (geometric area) is thereby significantly increased.

The type and form of the sensor-active material determines naturally the requisite sponge structure of the porous silicon which is produced by the etching treatment.

Basically one obtains after doping, different porosity profiles whereby in n-silicon, deep etching channels are formed which are provided with branches and whose mean pore diameter is determined by the selected parameters of pretreatment, temperature, composition of the electrolyte, anodization current density and anodization duration as well as posttreatment. By illumination, i.e. exposure to light, during the anodic etching treatment, the pore formation can be influenced, whereby, especially by intermittent light impingement optionally desirable diameter variations in pore passage over the length of the pore can be achieved.

The porous structure which results from etching of p-silicon as well as n+silicon or p+silicon (microporous or with so-called herring-bone branching) can be selected by the choice of the type of sensor-active material which is to be applied. A detailed collection of etching conditions and etching results can be found in R. L. Smith and S. D. Collins in J. Appl. Phys. 71 R1 of 1992.

One can distinguish, based upon the pore diameter of the produced sponge structure, between microporous silicon (pores of a diameter less than 2 nm), mesoporous silicon (pores of a diameter of 2–50 nm) and macroporous silicon (pores of a diameter greater than 50 nm). For the process parameters which can be varied for the etching treatment of the invention, use of the following especially can be made:

the electromechanical pretreatment of the semiconductive substrate (hydrofluoric acid, organic or inorganic solvents, water, as well as their mixtures);

the etching medium and solvent medium used (HF-ethanol or HF propanol mixtures);

the process temperature (5°–150° C.);

the anodization current (1–500 mA/cm$^2$);

the additional illumination during the anodization (wavelength $\lambda$=200–800 nm, intensity or power: 0.1–100 mW/cmz, distance of the lamp from the upper surface of the specimen or the specimen underside as well as the frequency of the illumination f=0.1–1000 Hz);

the posttreatment of the porous sponge structure (flushing regimen, e.g. in ethanol/temperature/storage conditions, e.g. in $N_2$ atmosphere).

The preferred nonconducting layer on the porous walls of the Si sponge structure to be generated can be $SiO_2$ or another dielectric component, like $Al_2O_3$ or $Ta_2O_5$ or $ZrO_2$, $Si_3N_4$ silicates, glasses, etc., individually or in combination. In the case of $SiO_2$, the Si surface provided in the sponge structure is intentionally oxidized. This is preferably achieved by a uniform thermal, anodic, chemical or natural oxidation. The layer thickness of the resulting nonconductive layer can thus vary, depending upon the pore size, within the range of 1 to 100 nm.

In the case of $Al_2O_3$ or $Ta_2O_3$ the base metal (Al or Ta) is at least initially electrochemically deposited galvanically or deposited from the gas phase and then converted into the corresponding oxide. The deposition of oxidic dielectric compounds like $SiO_2$, $Al_2O_3$, $Ta_2O_5$, $ZrO_2$, $Si_3N_4$, etc. by conventional PVD processes or CVD processes directly upon a silicon substrate is also known (L. Bousse et al, Sensors and Actuators, Vol. 17 (1994), 157–164).

Sensor active materials which can be anchored in or on the so formed porous structure according to the invention are known in large number. For example, different systems are given below together with the suitable porosity of the silicon as well as the type of anchoring.

Apart from pure adsorption or chemisorption, it appears that a covalent bonding of sensor-active material to the porous structure is suitable when the mean pore diameter is selected between 10 and $10^3$ nm. The pore surfaces can be activated by chemical pretreatment or modification, e.g. silanization, for the bonding of sensor-active material. Furthermore, so-called functional cross linkers (spacer molecules) like, for example, glutaraldehyde, can be anchored to the pore boundary surfaces or walls.

A complete or partial cross-linking (for example only in the region close to the surfaces) between the biomolecules which are incorporated in the porous layer with one another, for example, with glutaraldehyde, can afford an especially stable integration of the biomaterials in the layer. Such a cross-linking can be achieved after incorporation of the biomolecules in the porous layer, for example, by exposure to a gluteraldealdehyde saturated atmosphere. The mean pore diameter of the so-treated layer should be greater than or approximately equal to 50 nm.

Biological structures, like enzymes, proteins, antibodies, cells, organelles, tissue segments, etc. can be incorporated directly or by means of gel inclusion, i.e. embedded in a carrier matrix of polymers, like polyurethane, polyacrylamide, agar-agar, gelatin, etc., optionally spatially cross-linked, whereby depending upon the size of the material to be included in the porous sponge structure, a mean pore size in the range of 10 nm to 100 $\mu$m, especially greater than or approximately equal to 20 nm, can be chosen.

For the anchoring of sensor-active materials in the form of liquid membranes, which, as "membrane cocktails," are comprised for example of polyvinylchloride, plasticizers, ion-active compounds (ionophores, and additives, pore sizes of at least 50 nm, preferably over 100 nm are provided.

Especially for chemosensors, glass layers are suitable which as liquid sol/gel layers+wetting agents are incorporated in the pores, with subsequent temperature treatment to an amorphous glass layer which can be suitable, dependent on the starting cocktail, for the detection of different alkali ions. For this purpose, pore sizes of greater than or approximately equal to 50 nm, especially in excess of 100 nm, are suitable. Solid layers of galvanically deposited metal or metal deposited from the gas phase and also electrochemically in the porous material, combined with metal compounds (like for example Ag/AgCl, etc.) which are useful for the detection of anions and have proved with the afore-described pore sizes to be extraordinarily flexible, whereby pore sizes in the range of 1– to 500 nm are especially suitable.

The sensor substances which are chosen can, in known manner, be combined from different sensor types: further details are found in the literature, for example in F. Sheller, F. Shubert, "Biosensors", Academy Publishers, Berlin 1989.

BRIEF DESCRIPTION OF THE DRAWING

The above and other objects, features, and advantages will become more readily apparent from the following description, reference being made to the accompanying drawing in which.

SPECIFIC DESCRIPTION

Figure 1A:
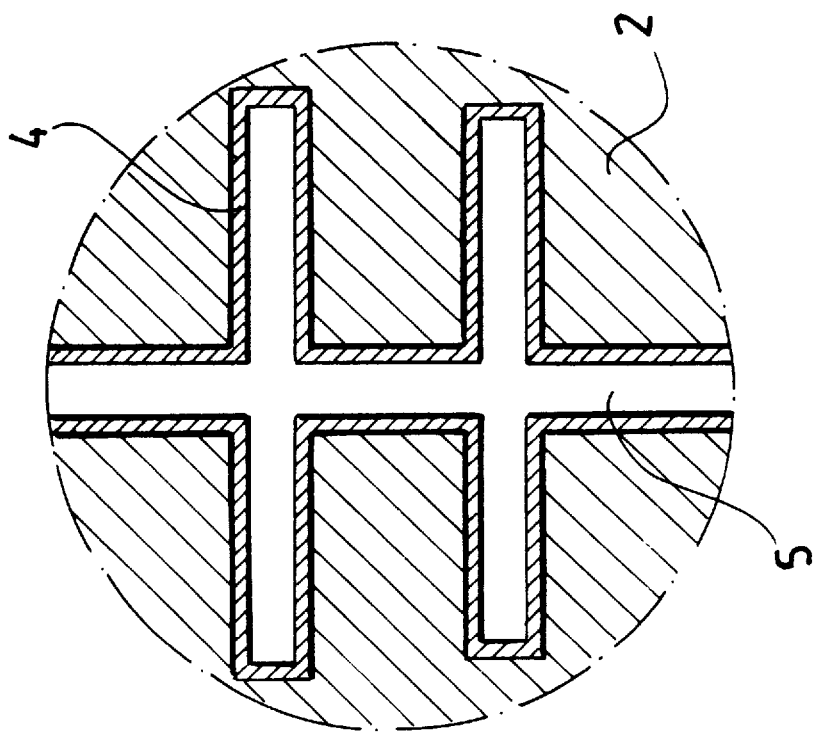
FIG. 1, and 1a are cross sections of a porous (bio) chemical silicon sensor, FIG. 1a being an enlargement of a portion of FIG. 1.
Figure 1:
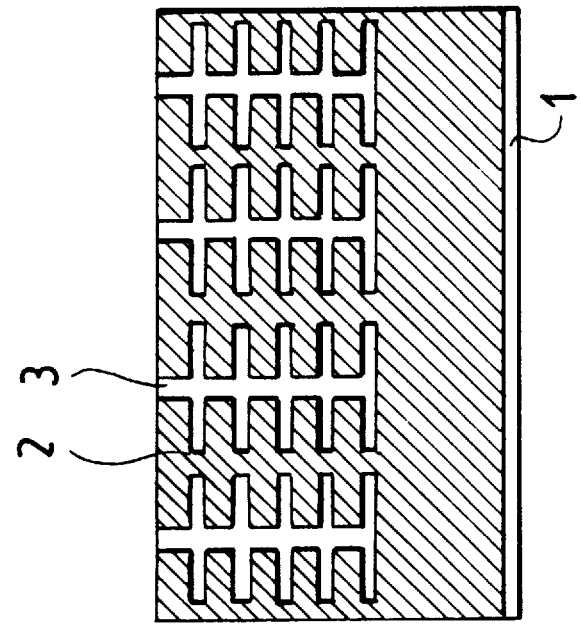

FIG. 1 and 1a shows in cross section the layer structure of the porous (bio)chemical silicon sensor.

As the base material 2, a doped monocrystalline or polycrystalline silicon is used. The doping concentration varies in the range between $1 \times 10^{14} - 1 \times 10^{18}/cm^3$ for n- or p-silicon and is greater than $1 \times 10^{18}/cm^3$ for n+- or p+-silicon. The underside of the base material 2 has an ohmic backside contact 1 comprised of a conducting layer or layer sequence, of for example Al, Ti/Pt/Au, Cr/Sb/Au or a similar conducting combination. This contact layer can be produced by means of conventional coating processes, like PVD deposition and ion implantation or by electrochemical deposition processes.

To produce the porous layer structure, the base substrate is built into a chemically inert sample cell (for example of Teflon) and the probe is connected as an anode against a cathode immersed in the etching solution, the cathode being for example of platinum, and a sponge or foam structure 3 generated in the following manner:

(a) If n-silicon is used as a starting material, depending upon the illumination intensity and the side of illumination, different types of pore structure and channel structure can result. If the source, for example, a halogen lamp, is on the side opposite side 1, in the bulk of the n-silicon, vertical macroporous channels are formed (length corresponding to the layer thickness of the porous structure, diameter: 0.1 to 10 $\mu$m) with horizontal lateral branchings 3, i.e. so-called side branches of comparable dimensions. Thereabove, there is formed in the surface region a microporous layer as isotropic pore structure (diameter: less than 5 nm), which in combination with the macroporous foam structure 3 is used or after the conclusion of processing can be removed with a NaOH solution. Both the energization current density (increase in the porosity) and also the treatment time (increase in the layer thickness of the porous silicon structure) determine the configuration of this macroporous sponge structure. The layer thickness of the microporous layer parallel thereto is substantially determined by the light penetration depth, i.e. the wavelength of the illumination source.

If the intensity of the illumination source is changed, in addition, with time, i.e. if during the pore growth for example, the light source is switched on and off, then the diameter of the vertical passage is additionally modified. During the illumination phase another pore diameter is formed than during the period of the dark phase. The result is a wave-like bulgy vertical pore and channel structure which supports the mechanical anchoring of the specifically disposed sensor membrane. If the light source is found on the side 1, the macropores are formed as vertical passage structures without laterally branchings. Depending upon the process parameters, the pore diameter then varies between 100 nm and 10 $\mu$m. The length of these vertical passages lies in the range of the total layer thickness of the porous layer.

(b) In contrast thereto, n-silicon forms a mesoporous foam structure (pore diameter: 2–50 nm, passage length corresponding to the layer thickness of the porous structure). The horizontal branchings do not extend strictly orthogonal to the vertical passages. The porous layer structure is comparable to a herring-bone pattern, i.e. the side branches are inclined by less than 45° with respect to the vertical passages.

(c) Microporous layer structures (mean pore diameter less than 2 nm) can be realized above all with p-silicon as the starting material. In this case, there is formed an isotropic homogeneously distributed pore structure. The pore diameter can in the above-indicated range be set by the illumination. The porosity is adjustable by variation of the anodization current.

(d) If a p+-doped silicon is used as the base material, the thus produced foam or sponge structure is comparable with the results for n+-doped silicon. The horizontal transverse branching corresponds entirely analogously in its dimensions to the construction described under (b). Moreover the vertical pore diameter as well as the passage lengths are comparable in their geometric extents.

The foam or sponge structure which can be variably set under points (a)–(d), opens up the possibility of a targeted tailoring of the sensor active (bio-)chemical membrane. For this purpose, the foam structure 3 (shown in FIG. 1a) is coated with a nonconductive material 4. The thus formed porous layer serves to receive the sensor-active components 5.

Depending upon the respective function, the sensor-active material can, as has already been described at the outset, be provided in the form of an ion selective membrane or also in the form of biosensor elements, whereby, depending upon requirements, a chemical pretreatment (for example by silanization) can be provided to produce a good, direct bonding of the sensor materials on or in the porous layer:

(a) The known production of ion selective membranes can be transferred in the same type and manner also to the porous foam structure. For this purpose, membrane material contained in a solvent (for example ionophore, plasticizer, PVC matrix) can be incorporated in the foam structure in which, after evaporation of the solvent, a stabilization and solidification occurs.

(b) Alternatively there is a further possibility of depositing biomolecules in the form of enzymes, antibodies-antigens, tissue segments, organelles or receptors as sensor-active membrane components or directly in the foam structure. For this purpose, physical (e.g. adsorption, gel inclusion) and also known chemical immobilization processes (e.g. covalent bonding, cross linking) can be used.

Figure 2:
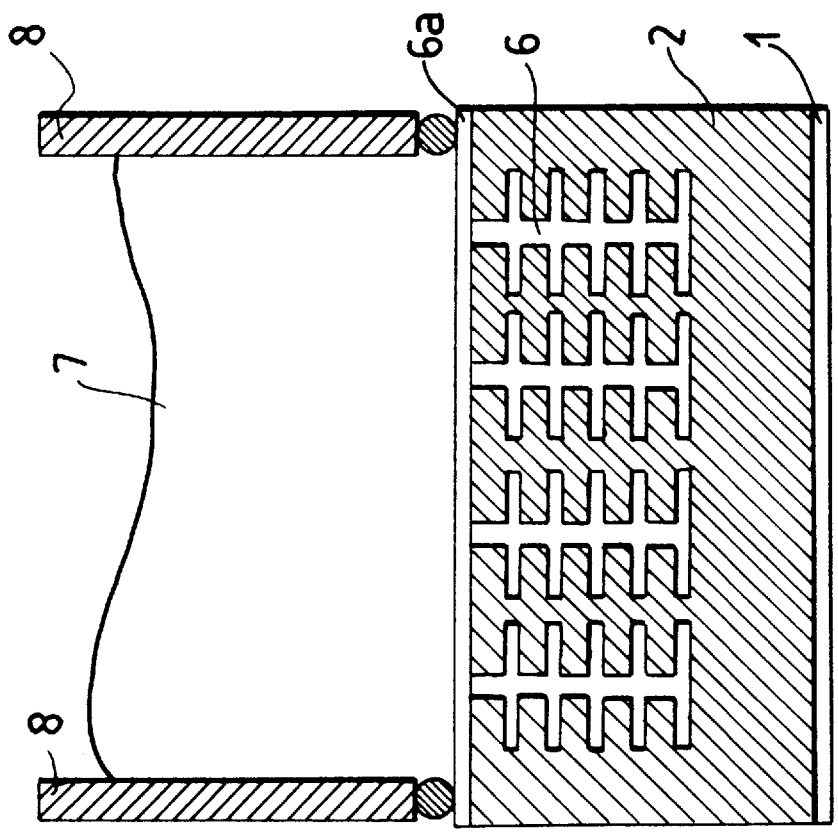
FIG. 2 is a section of a capacitative field effect sensor.

FIG. 2 shows, as an example, the production of a (bio-) chemical porous capacitive field effect sensor. The layer structure corresponds to the arrangement described in FIG. 1. The sensor active material 6, optionally provided in the form of a membrane, can function both as a chemosensor and also as a biosensor depending upon the respective layer composition. Furthermore, there is a possibility that sensor-active materials 6 will deposit in the foam structure and optionally additionally on the sensor surface. The porous sensor element is encapsulated in an appropriate measurement cell 8 (for example of Teflon or PMMA) and is brought directly into contact with the analyte solution 7. It is also conceivable to provide an encapsulation which corresponds to the construction shown in FIG. 3 and described below.

To produce the electrical connection between the anolyte cells 7 and the metallic substrate contact 1, for example, a constant potential commercially available reference electrode can be incorporated in 7 and connected with 1. Instead of the latter, it is also possible to use an identical nonsensitive porous sensor element as the reference element. In this case, there is the advantage of an arrangement primarily in miniaturization which as a rule is limited by the size of the reference electrode and with a reduced effect of external influences like, for example, different temperature coefficients of the sensor element and the reference electrode.

Figure 3:
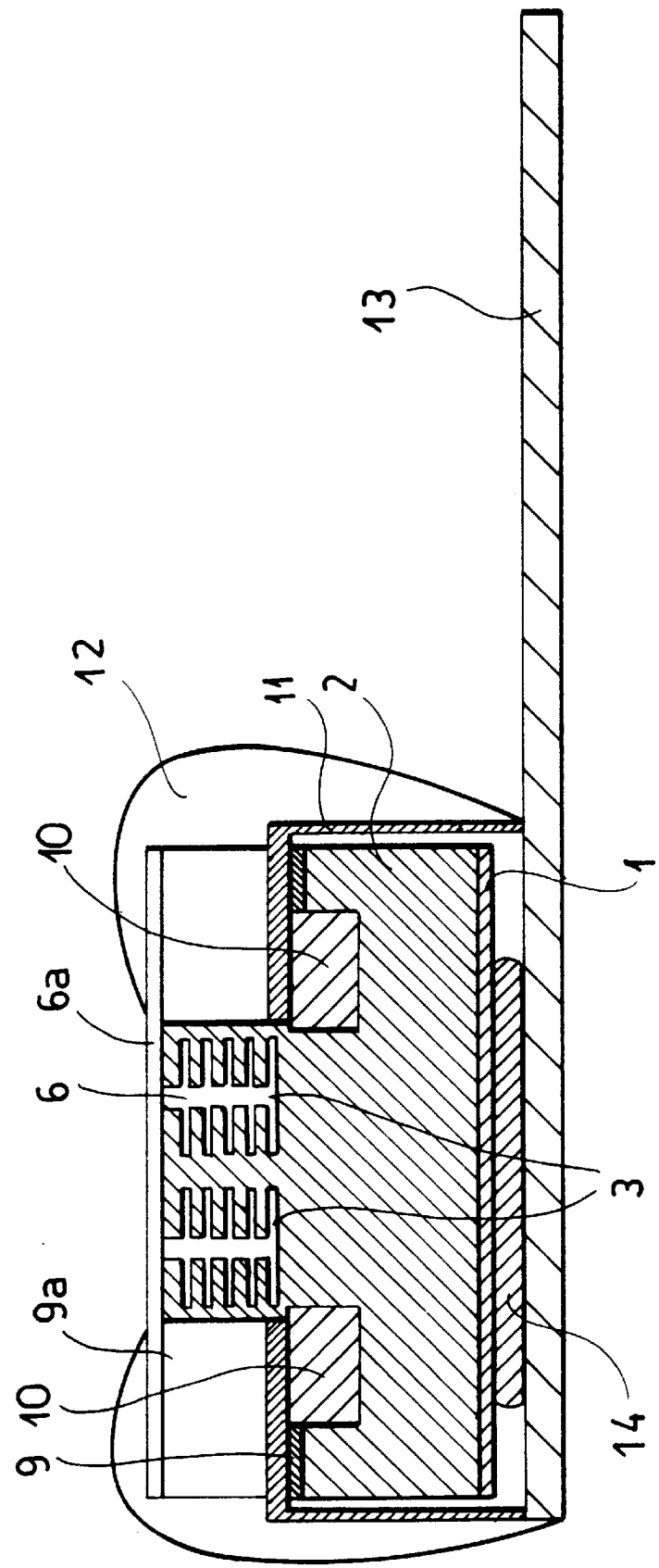
FIG. 3 is a section through a field effect sensor.

FIG. 3 shows the construction of a porous (bio-) chemical field effect transistor. The base material used corresponds to that of the above-described capacitive silicon sensor. Depending upon the doping of the base material 2, the two pockets, source and drain 10, have the opposite doping. If the base material is n-doped, the source and drain are p-doped and vise versa. These are connected with a fixed support, for example, a printed circuit board substrate 13, via a metal contact 11 (for example Ti/Al, Ti/Pd/Au, or other conducting material). The metallization 11 is insulated from the base substrate by an insulator layer or layer sequence 9 and 9a of $SiO_2$ or $SiO_2/Si_3N_4$ or $SiO_2/Al_2O_3$ or $SiO_2/Ta_2O_5$ etc. The production of such field effect transistors is known from the literature (K. Horninger, Integrated MOS Circuits, Springer Verlag (1987) Heidelberg).

New in this arrangement is the use of the gate region between the two pockets 10 in the form of a porous silicon gate. For that, during the appropriate processing, i.e. directly after the doping of both pockets 10, a "projecting" gate is produced as shown in the Figure, for example by an additional photolithographic and etching step. Alternatively, such a gate can be realized also by means of a process used in semiconductive technology like, for example, epitaxy, etc.

The generation of the foam structure 3 in the silicon starting material or subsequent deposition of the sensor active material in conjunction therewith are effected in exactly analogous manner as described in FIG. 1. The substrate contact 1 for the base carrier 13 is realized by a conductive adhesive bonding 14, for example, with conductive silver. The sensor component is protected with a protective layer 12, of for example, epoxy resin or another potting material against the measurement environment so that only the sensor active gate region can contact the anolyte solution. The encapsulation can, however, also be effected by means of incorporation in a fixed probe cell as described in FIG. 2. The possibility, similar to that of the capacitive porous (bio-)chemical sensor to introduce a non-sensitive sensor element directly instead of an external reference electrode is also a solution with this construction, the reference electrode having the form of a reference transistor.

Figure 4:
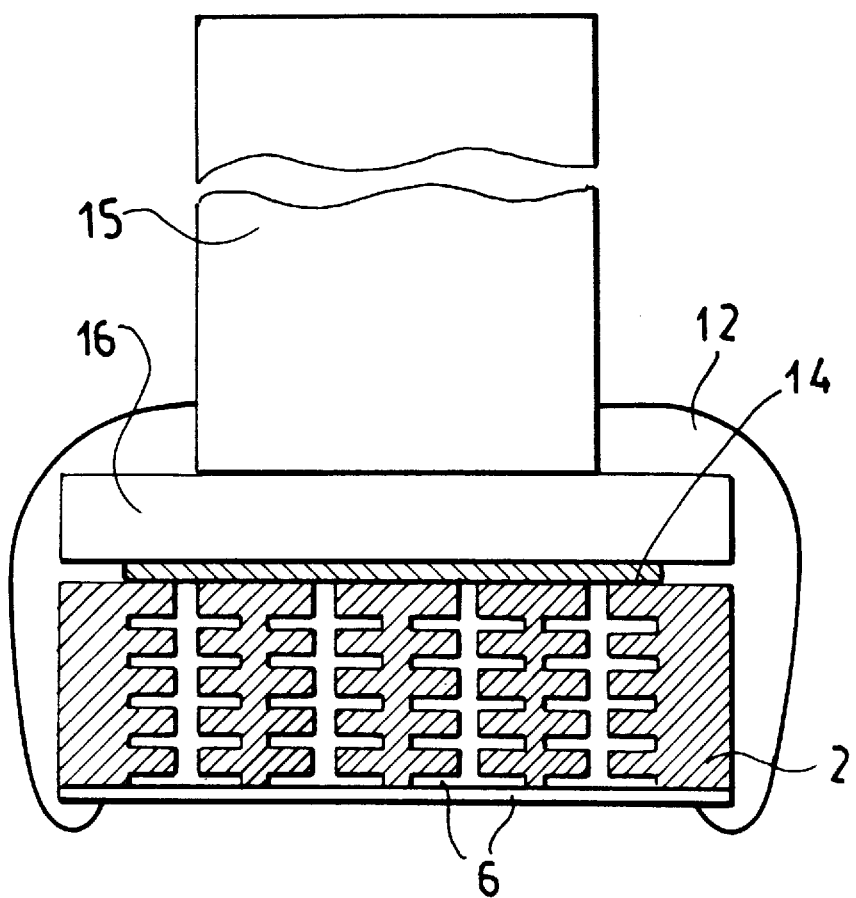
FIG. 4 is section through a potentiometrically operating ion selective electrode (ISE)

An embodiment in the form of a porous potentiometric (bio-)chemical ion selective electrode (ISE) is apparent from FIG. 4. The production of the porous foam structure and its sheathing with a nonconductive material is effected in an analogous way to that described under FIG. 1. In connection therewith, the base substrate 2 from the probe back side 1 is etched away until the region of the foam structure by a wet chemical process, for example by means of a HF/water mixture, so that the foam structure is liberated on the back side of the probe.

Figure 4A:
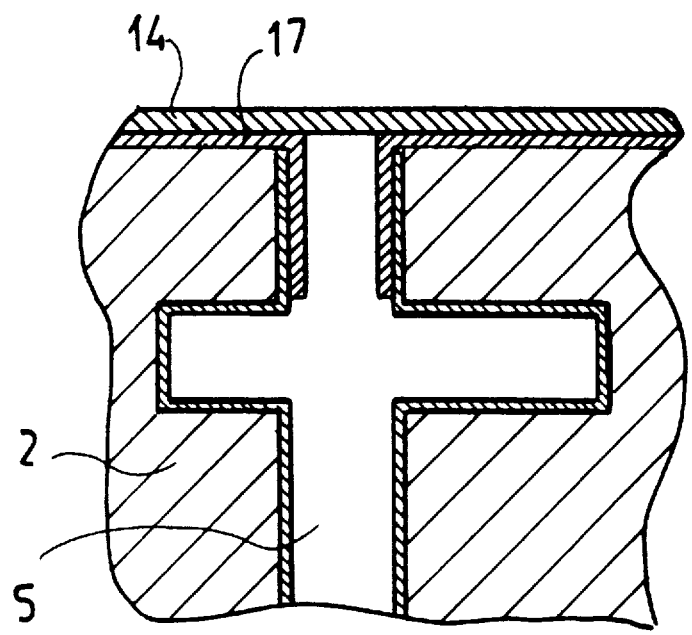
FIGS. 4A and 4B are sections of details of other embodiments.
Figure 4B:
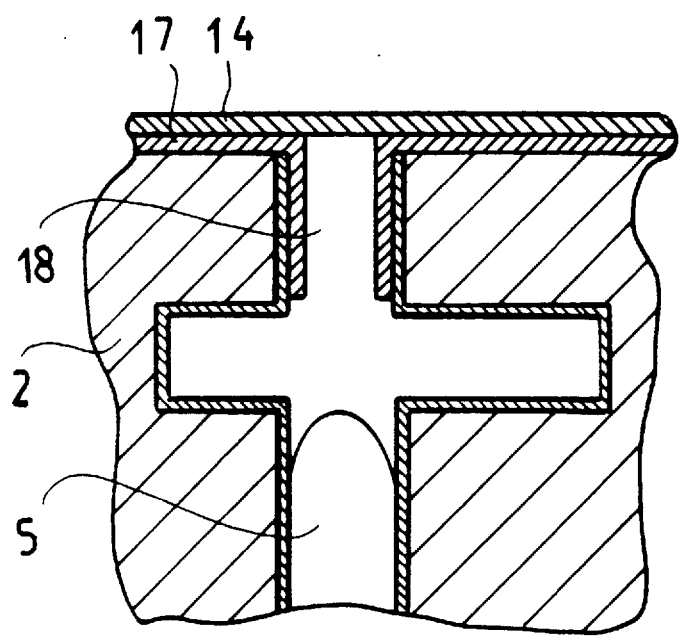

Before the sensor active components 6 as solid or liquid electrolyte in an exactly analogous way as described under FIG. 1, are incorporated in the foam structure, the metallic conductors must be realized as is indicated in FIGS. 4A or 4B. Thus in FIG. 4A a metal film 17, for example of Ag, is deposited in the pore structure by means of conventional PVD processes, (for example by evaporation). The chloridization of this Ag layer by means of known electrochemical processes is effected directly following. An additional internal electrolyte is introduced in FIG. 4B. This comprises as a rule a high molecular salt solution, for example saturated KCl solution which remains as an internal electrolyte after evaporation of the solvent when introduced in a solid organic matrix, for example, gelatin.

The so processed semiconductive structure is fixed by means of a conductive adhesive bond 14, e.g. conductive silver on a carrier 16 (FIG. 4) with electric contacts, for example from glass, plastic, silicon or ceramic. The thin porous silicon structure is thereby stabilized on the carrier 16. The processing of the sensor active layer is effected as has already been set out under FIG. 1. The completed porous ISE is applied to a holder 16 of solvent resistant material with electric contacting, for example, Teflon or plastic. The sensor component is protected against the measurement environment by means of a protective layer 12 of, for example, epoxy resin so that only the sensor active region of the porous ISE contacts the anolyte solution.

Figure 5:
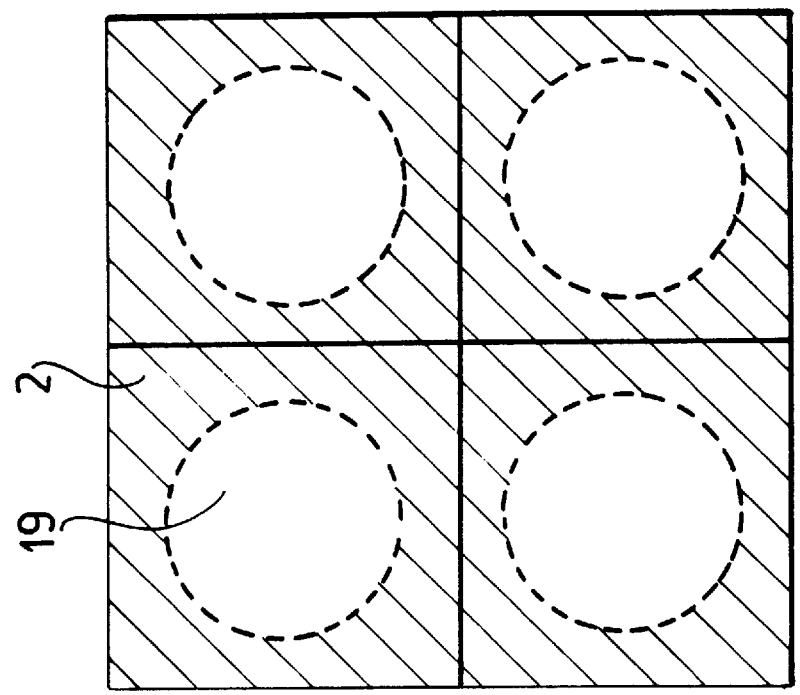
FIG. 5 is a section showing a sensor array.

FIG. 5 shows the arrangement of a (bio-)chemical porous semiconductor sensor as a multisensor in the form of a sensor array arrangement. Here are illustrated porous sensors 19 of different sensitivity within one silicon substrate 2. Thus in a first step via a simple photolithographic structuring the number of sensor elements (for example four variable sensors) is established. Thereafter, the individual porous foam structures corresponding in number are produced by the above-indicated process steps to sensor elements. Depending upon the respective use, sensor elements as described in FIG. 2, FIG. 3, FIG. 4 are realized. The sensor elements are encapsulated or incorporated in a fixed housing entirely analogously in kind and manner in a probe cell.

We claim:

1. A chemical sensor which comprises:
    a body of silicon etched from an active surface thereof to form a pore network penetrating into said body from said active surface and forming a foam structure from said body at least along said surface;
    a layer of at least one reactive material in said foam structure and lining pores thereof, whereby said layer can contact and react with an environment to alter conductivity characteristics of said body; and
    at least one electrode in contact with a surface of said body opposite said active surface for electrical measurement of altered conductivity of said body, said pores having pore openings selected to enable said pores to accommodate said material.

2. The chemical sensor defined in claim 1, further comprising a boundary layer on walls of said pores between said body of silicon and said reactive material, said boundary layer having a thickness of substantially 1 to 100 nm and being selected from the group consisting of silicon dioxide, aluminum oxide, tantalum oxide, silicon nitride and mixtures thereof.

3. The chemical sensor defined in claim 1 wherein said foam structure has a thickness of 10 mm to 100 $\mu$m and said pores are passages with branches having a mean pore diameter of 1 nm to 10 $\mu$m.

4. The chemical sensor defined in claim 1 wherein said reactive material is adsorbed on said body of silicon in said pores.

5. The chemical sensor defined in claim 1 wherein said reactive material has biologically active molecules cross linked to a substance in said pores.

6. The chemical sensor defined in claim 1 wherein said reactive material is a biologically active material distributed within a layer former constituted as glass or a polymeric membrane.

7. The chemical sensor defined in claim 1 constituted as an element of an ion selective electrode.

8. The chemical sensor defined in claim 1 constituted as an element of a capacitative field effect transistor.

9. The chemical sensor defined in claim 1 wherein said sensor is part of an array of said sensors with each of said sensors being of a sensitivity different from that of others of said sensors.

10. A method of making a chemical sensor which comprises the steps of:
   a) etching a body of silicon from an active surface thereof to form a pore network penetrating into said body from said active surface and forming a foam structure from said body at least along said surface with a thickness of 10 nm to 100 μm, said pore structure being constituted of branched pores having a mean pore diameter of 1 nm to 10 nm;
   b) lining said pores with a nonconducting boundary layer selected from the Group which consists of silicon dioxide, aluminum oxide, tantalum oxide, silicon nitride and mixtures thereof, said boundary layer having a thickness of 1 to 100 nm;
   c) depositing in said pores at least one reactive material in a layer which can contact and react with an environment to alter conductivity characteristics of said body; and
   d) applying to said body at least one electrode in contact with a surface of said body opposite said active surface for electrical measurement of altered conductivity of said body, said pores having pore openings selected to enable said pores to accommodate said material.

11. A method of making a chemical sensor defined in claim 10, further comprising the step of forming said material by incorporating a bioactive substance in a layer forming material selected from the Group which consists of glass and polymers.

* * * * *